US00PP32815P2

(12) United States Plant Patent
Moon

(10) Patent No.: US PP32,815 P2
(45) Date of Patent: Feb. 16, 2021

(54) ***CARPINUS* TREE NAMED 'CCMTF1'**

(50) Latin Name: *Carpinus caroliniana*
Varietal Denomination: CCMTF1

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 16/602,871

(22) Filed: Dec. 13, 2019

(51) Int. Cl.
*A01H 5/00* (2018.01)
*A01H 6/00* (2018.01)

(52) U.S. Cl.
USPC ..... Plt./216

(58) Field of Classification Search
USPC ..... Plt./216, 226
CPC ... A01H 5/02; A01H 5/04; A01H 6/00; A01H 5/00
See application file for complete search history.

*Primary Examiner* — June Hwu
(74) *Attorney, Agent, or Firm* — Cassandra Bright

(57) ABSTRACT

A new and distinct *Carpinus caroliniana* tree named 'CCMTF1' is disclosed, characterized by bright green young foliage, dark green mature foliage and yellow Fall foliage. Tree shape is distinctively upright pyramidal. The new variety is a *Carpinus* tree, typically used for landscapes and gardens.

3 Drawing Sheets

Latin name of the genus and species: *Carpinus caroliniana.*

Variety denomination: 'CCMTF1'.

BACKGROUND OF THE INVENTION

The new cultivar is a product of chance discovery. The new variety was discovered growing as a seedling among a group of crossbred *Carpinus caroliniana* at a tree farm in Loganville, Ga. The inventor made this discovery in Spring 2014. The exact seed and pollen parents cannot be identified.

Asexual reproduction by grafting of the new cultivar 'CCMTF1' was first performed during the Summer of 2014 at a farm in Washington, Ga. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that the new variety represents a new and improved variety of *Carpinus caroliniana* tree as particularly evidenced by the pyramidal growth habit with a strong central leader, its full scaffolding branch structure, and its deep, dark green lustrous foliage in summer and bright lustrous yellow leaves in the fall. These genetic traits can be consistently reproduced by asexual propagation.

SUMMARY OF THE INVENTION

The cultivar 'CCMTF1' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CCMTF1' grown in Washington, Ga. These characteristics in combination distinguish 'CCMTF1' as a new and distinct *Carpinus caroliniana* cultivar:

1. Upright form, with pyramidal growth and a dominant central leader.
2. Bright green flush foliage in contrast with dark green mature foliage.
3. Bright yellow fall color.
4. Rapid growth, approximately 1 inch of caliper growth per growing season and 3.5 to 4 feet in height.
5. Full scaffolding branch structure.

PARENT COMPARISON

The exact parent varieties cannot be identified.

COMMERCIAL COMPARISON

Plants of the new cultivar 'CCMTF1' are similar to plants of *Carpinus caroliniana* 'CCSQU', U.S. Plant Pat. No. 11,280, in most horticultural characteristics, however, plants of the new cultivar 'CCMTF1' differ in the following:

1. The new variety has an upright pyramidal growth habit with strong scaffolding, while this comparator has a tight upright growth habit.
2. The new variety has a bright green Spring foliage flush in contrast to dark mature foliage, while this comparator has dark green foliage Spring through Summer.
3. Foliage of the new variety falls off intermittently, while foliage of this comparator falls off uniformly in the Fall.

Plants of the new cultivar 'CCMTF1' are similar to plants of the unpatented commercial variety, *Carpinus caroliniana* 'Uxbridge' in most horticultural characteristics, however, plants of the new cultivar 'CCMTF1' differ in the following:

1. The new variety has an upright, pyramidal growth habit with dominant central leader, while this comparator is upright and narrow.
2. The new variety has bright yellow fall foliage, while this comparator has brighter red and orange fall foliage.

Plants of the new cultivar 'CCMTF1' are similar to plants of the unpatented commercial variety, *Carpinus caroliniana* 'J.N. Globe' in most horticultural characteristics, however, plants of the new cultivar 'CCMTF1' differ in the following:

1. The new variety has an upright pyramidal growth habit, while this comparator has a compact globe form.
2. New variety has bright yellow fall foliage, while this comparator has orange-red fall color.
3. New variety grows faster than this comparator.

Plants of the new cultivar 'CCMTF1' are similar to plants of the unpatented commercial variety, *Carpinus caroliniana* 'JFS-KW6' in most horticultural characteristics, however, plants of the new cultivar 'CCMTF1' differ in the following:

1. The new variety has an upright pyramidal growth habit with dominant central leader, while this comparator is upright.
2. New variety has bright yellow fall foliage, while this comparator has red fall foliage.
3. Leaves of this comparator hold fall color longer than the new variety.

Plants of the new cultivar 'CCMTF1' are similar to plants of the unpatented commercial variety, *Carpinus caroliniana* 'J.N. Upright' in most horticultural characteristics, however, plants of the new cultivar 'CCMTF1' differ in the following:

1. The new variety has an upright, pyramidal growth habit with dominant central leader, while this comparator is upright and narrow.
2. New variety has bright yellow fall foliage, while this comparator has orange-red fall color.

Plants of the new cultivar 'CCMTF1' are similar to plants of the unpatented commercial variety, *Carpinus caroliniana* 'Pyramidalis' in most horticultural characteristics, however, plants of the new cultivar 'CCMTF1' differ in the following:

1. The new variety has an upright, pyramidal growth habit with dominant central leader, while this comparator is v-shaped with rounded top.

Plants of the new cultivar 'CCMTF1' are similar to plants of the unpatented commercial variety, *Carpinus caroliniana* 'Schmidt #6' in most horticultural characteristics, however, plants of the new cultivar 'CCMTF1' differ in the following:

1. New variety has bright yellow fall foliage, while this comparator has bright red fall color.

Plants of the new cultivar 'CCMTF1' are similar to plants of the unpatented commercial variety, *Carpinus caroliniana* 'Stowe Cascade' in most horticultural characteristics, however, plants of the new cultivar 'CCMTF1' differ in the following:

1. The new variety has an upright, pyramidal growth habit with dominant central leader, while this comparator has an arching, weeping form.

BRIEF DESCRIPTION OF THE PHOTOGRAPHS

The accompanying photograph in FIG. 1 illustrates deciduous trees during Winter in a field. The full scaffolding structure can be seen.

Figure 1:
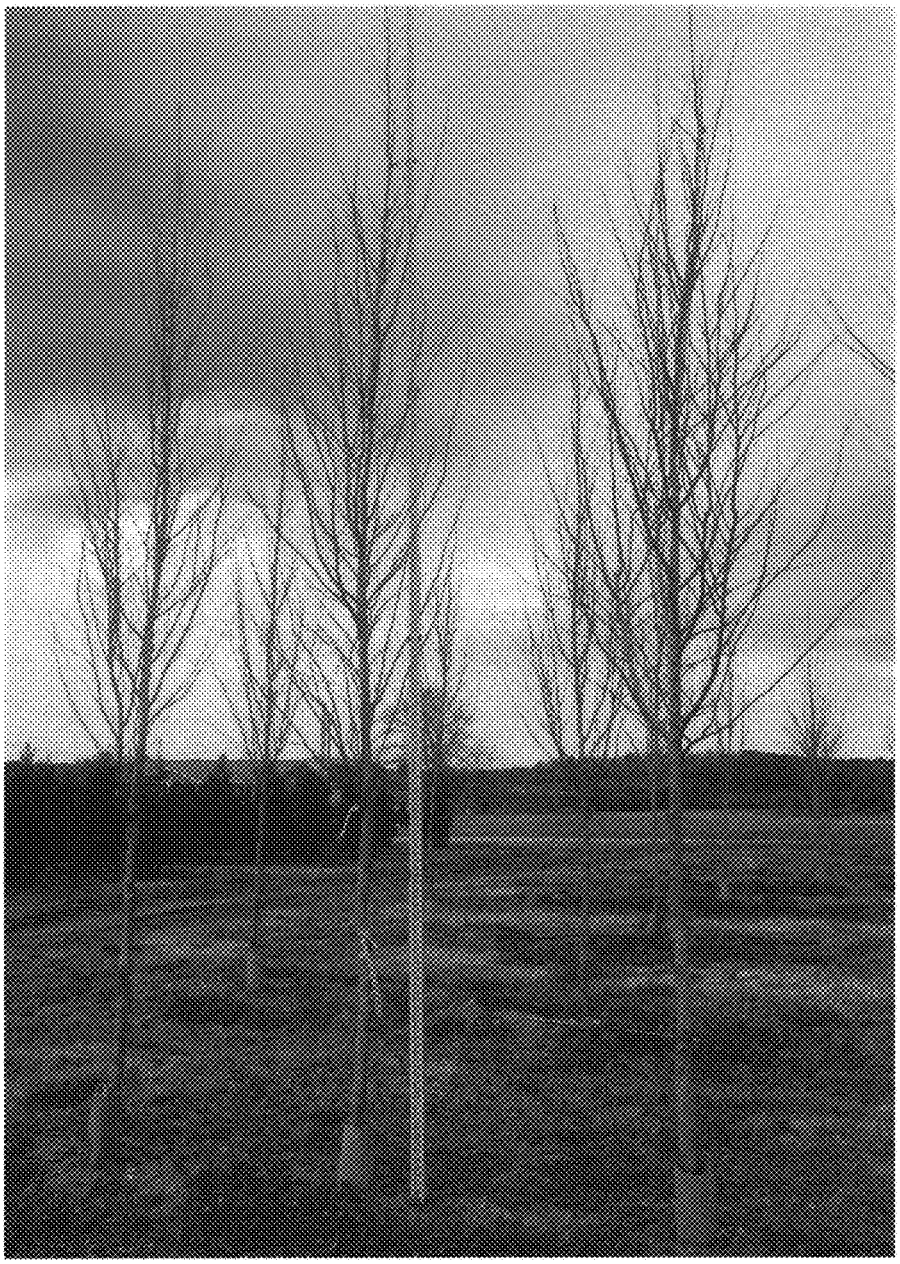
Figure 2:
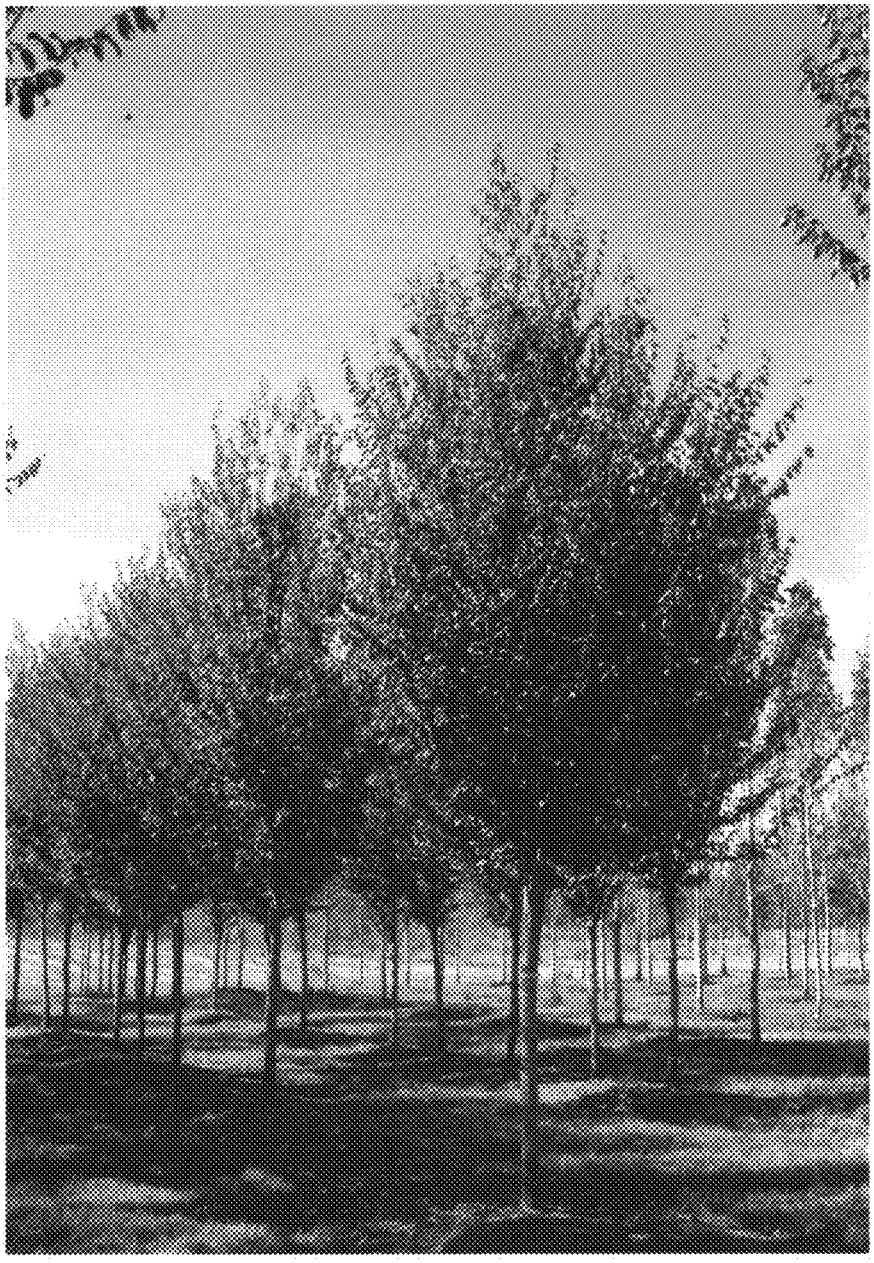
FIG. 2 illustrates a field of trees of the new variety during early Summer, foliage color and the natural tree shape are illustrated.
Figure 3:
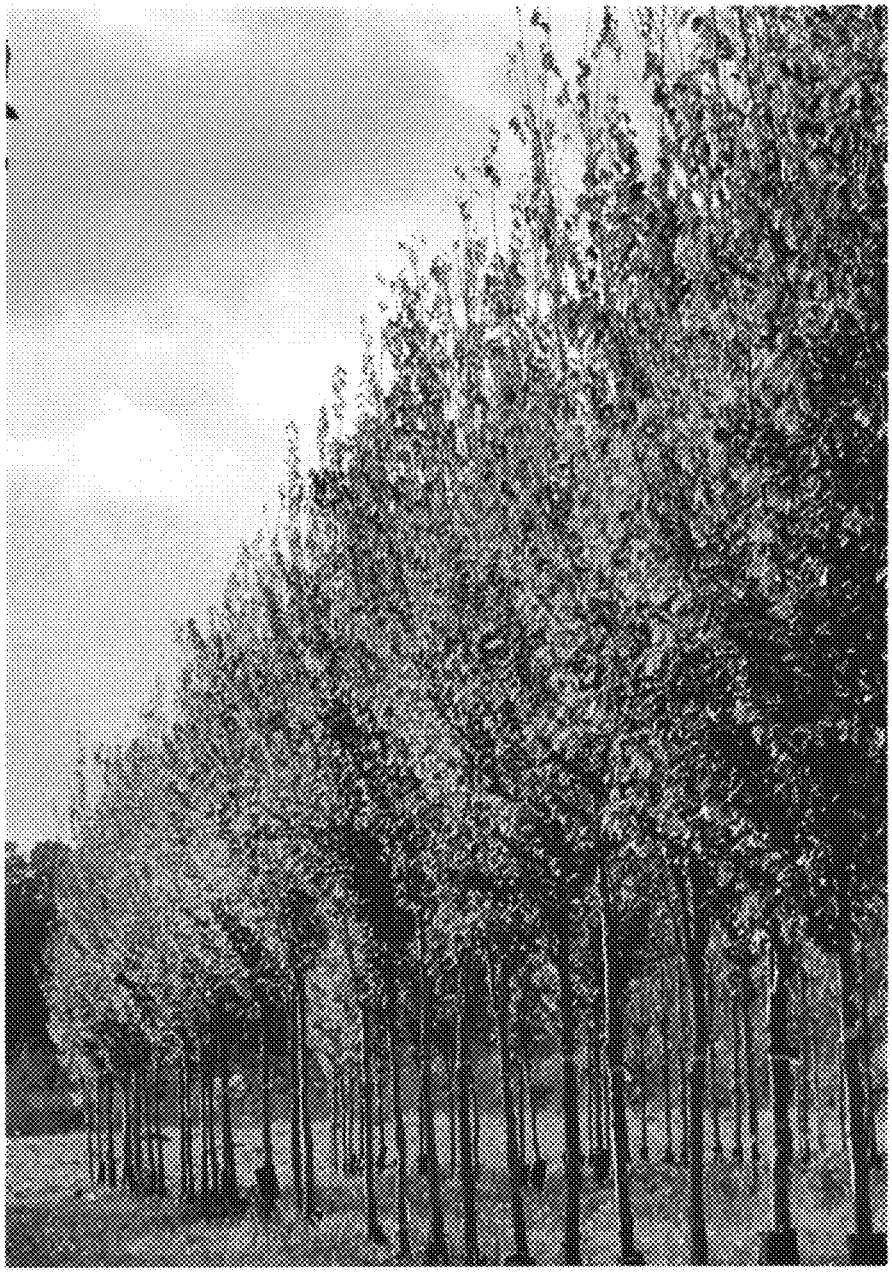
FIG. 3 illustrates a field of trees during late Fall, showing yellow foliage of 'CCMTF1'.

All trees illustrated are field grown in Washington, Ga. Trees in FIGS. 1, 2 and 3 are approximately 3 years from planting into the field, 4 years old from grafting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CCMTF1' plants grown outdoors and in a nursery in Washington, Ga. Plants are approximately 2 years old, in a 3 gallon nursery container. Temperatures ranged from 5° C. to 10° C. at night to 18° C. to 27° C. during the day. Measurements and numerical values represent averages of typical plant types.

Botanical classification: *Carpinus caroliniana* 'CCMTF1'.

PROPAGATION

Cleft grafting:

Root description: Woody. Brown roots not accurately measured with an R.H.S. Colour Chart.

PLANT

Growth habit: Upright pyramidal tree.

Height: Approximately 12 to 15 feet at 3 years.

Spread: Approximately 12 to 15 feet at 3 years.

Aspect and angle: Branches at acute angles, 45 degrees or less.

Growth rate: Rapid, approximately 1 inch of caliper growth per growing season and 3.5 to 4 feet in height.

Trunk characteristics:

- *Diameter*.—About 4 inches measured at approximately 3 inches above soil level at 4 years.
- *Color*.—Near RHS Greyed-Green 198A with large blotches 197A and 197B.
- *Surface texture*.—Rippled.
- *Lenticels present*.—Yes. Inconspicuous, round.
- *Lenticel length*.—Less than 0.5 mm.
- *Lenticel diameter*.—Less than 0.5 mm.
- *Lenticel density*.—Moderate.
- *Lenticel color*.—Near RHS Greyed-Green 198D.

Stem characteristics:

- *Length*.—Average Range 30 to 65 cm.
- *Diameter*.—Average 7 mm.
- *Color*.—Near RHS Greyed-Purple N187A.
- *Surface texture*.—Dense lenticels, about 1 mm long and less than 1 mm wide. Colored near White N155A.

FOLIAGE

Leaf:

- *Arrangement*.—Alternate.
- *Shape*.—Ovate.
- *Average length*.—Approximately 8 cm excluding petiole.
- *Average width*.—Approximately 5 cm.
- *Apex*.—Acute.
- *Base*.—Obtuse or asymmetrical cordate.
- *Margin*.—Double serrate. Secondary serration minute. Primary serration regular, at intervals about 8 to 10 mm.

*Texture of top surface*.—Glabrous.

*Texture of lower surface*.—Glabrous.

*Color*.—Young foliage: Upper side: Near RHS Yellow-Green N144B. Under side: Near RHS Yellow-Green 145A. Mature foliage: Upper side: Near RHS Green 137A. Under side: Near RHS Green 138A. Fall foliage: Upper side: Near RHS Yellow 13A. Under side: Near RHS Yellow 13C.

*Venation*.—Type: Pinnate. Color: Venation color upper side: Near RHS Yellow-Green 144C. Venation color under side: Near RHS Yellow-Green N144A.

*Petiole*.—Length: Average 9 mm. Diameter: Average 2 mm. Color: Upper side: Near RHS Yellow-Green 144A. Under side: Near RHS Yellow-Green 144C.

*Leaf bud*.—Narrow deltoid, about 5 mm long and 3 mm at widest point. Colored near Greyed-Orange 175A.

FLOWER

Flowering begins: Around early Spring in Georgia. Individual male and female catkins.

Male catkins: About 3 to 6 cm long, about 5 to 8 mm wide. Weeping. Colored near RHS Yellow-Green 145A, turning Yellow-Green 154C flushed Greyed-Red 181B.

Female catkins: Paired, about 2 cm long and approximately 4 mm wide. Colored near Yellow-Green 149D.

REPRODUCTIVE ORGANS

Reproductive organs minute, less than 1 mm and irregularly formed:

Androecium:

*Number*.—Typically 3 stamens per flower.

*Length*.—About 5 mm.

*Color*.—Near Yellow-Green 145C.

Gynoecium:

Pistil:

*Number*.—1.

*Length*.—9 mm.

*Style*.—Length: 5 mm. Color: Near Yellow-Green 154D.

*Stigma*.—Shape: Linear. Color: Near Greyed-Orange 163D.

OTHER CHARACTERISTICS

Disease/pest resistance: Neither resistance nor susceptibility to normal diseases and pests of *Carpinus* has been observed.

Drought resistance: No tolerance for drought.

Temperature tolerance: USDA Zones 4 through 8.

Fruits: Paired nutlets. Ovate, pubescent, about 7 mm long and 4 mm in diameter. Colored near Yellow-Green 144B. Nutlet scale 3-lobed, about 2 cm long and 1 cm wide. Immature nutlet scale colored near Yellow-Green N144B, turning papery and Grey-Brown 199C around October. Fall nutlet color near Grey-Brown Grey-Brown 199B.

What is claimed is:

1. A new and distinct cultivar of *Carpinus caroliniana* tree named 'CCMTF1' as herein illustrated and described.

* * * * *